United States Patent
Ishii et al.

(10) Patent No.: US 6,523,999 B1
(45) Date of Patent: Feb. 25, 2003

(54) PROCESS FOR EVALUATING LIFE OF ARTICLE SUBJECTED TO THERMAL CYCLES BASED ON COMPARISON OF STRAIN RATES MEASURED UNDER EVALUATING CONDITIONS AND ACTUAL SERVICE CONDITIONS

(75) Inventors: Kazuo Ishii, Saitama (JP); Makoto Nakada, Saitama (JP); Masaru Enomoto, Saitama (JP); Yasunori Konishi, Saitama (JP); Shinichi Takahashi, Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/658,115

(22) Filed: Sep. 8, 2000

(30) Foreign Application Priority Data

Sep. 10, 1999 (JP) .......................................... 11-256830

(51) Int. Cl.$^7$ .......................... G01N 3/60; G01N 25/72
(52) U.S. Cl. ............................ 374/57; 374/55; 374/47; 374/51; 374/5; 73/766; 702/34
(58) Field of Search .............................. 374/57, 55, 47, 374/5, 51, 49, 46, 45; 73/760, 866.4, 788, 789, 766, 808, 810; 702/34

(56) References Cited

U.S. PATENT DOCUMENTS

| | | | | |
|---|---|---|---|---|
| 3,908,447 A | * | 9/1975 | Salt .............................. | 73/789 |
| 3,950,985 A | * | 4/1976 | Buchwald et al. ............. | 702/34 |
| 4,947,341 A | * | 8/1990 | Shine ........................... | 73/760 |
| 5,042,295 A | * | 8/1991 | Seeley ........................ | 73/117.3 |
| 5,048,346 A | * | 9/1991 | Yano et al. .................... | 374/57 |
| 5,050,108 A | * | 9/1991 | Clark et al. ................... | 702/34 |
| 5,129,443 A | * | 7/1992 | Yano et al. ................... | 374/57 |
| 5,291,419 A | * | 3/1994 | Satoh et al. .................. | 702/34 |
| 5,967,660 A | * | 10/1999 | Akpan et al. .................. | 374/57 |
| 5,980,103 A | * | 11/1999 | Ikuno et al. ................... | 374/57 |
| 6,260,998 B1 | * | 7/2001 | Garfinkel et al. ............. | 374/57 |
| 6,383,310 B1 | * | 5/2002 | Otsuka et al. ............... | 148/327 |

OTHER PUBLICATIONS

"Thermal Fatigue Properties and Estimate of Thermal Fatigue Life for Materials Used in Automotive Engine Exhaust Components", Kimura et al, *Hitachi Metal Technical Report*, vol. 8, pp. 79–84. (Date Unavailable, Prior to Sep. 8, 2000).

"Thermal Strain Analysis of Exhaust Manifold Using Measured Temperature", Kudo et al, pp. 81–84 (Date Unavailable, Prior to Sep. 8, 2000).

* cited by examiner

*Primary Examiner*—Diego Gutierrez
*Assistant Examiner*—Stanley J. Pruchnic, Jr.
(74) *Attorney, Agent, or Firm*—Arent Fox Kintner Plotkin & Kahn, PLLC

(57) ABSTRACT

A method to accurately evaluate a thermal cycle life of an article with a restraint rate as an evaluating parameter without providing a thermal cycle under actual service conditions to the article subjected to the thermal cycle. A thermal cycle of a temperature profile under evaluating conditions, is provided to the article, so that a temperature profile under actual service conditions and the temperature profile under the evaluating conditions satisfies the following condition expression, and the thermal cycle life of the article to be subjected to the thermal cycle under the actual service conditions is evaluated, based on the restraint rates determined in the temperature profile, $$\|[t(x)-t_0]/[t(x=i)-t_0]-[T(x)-T_0]/[T(x=i)-T_0]\| < E$$

wherein $[t(x)-t_0]/[t(x=i)-t_0]$ is a standardized temperature profile under the actual service conditions; $[T(x)-T_0]/[T(x=i)-T_0]$ is a standardized temperature profile under the evaluating conditions; and E is a predetermined value.

2 Claims, 10 Drawing Sheets

PROCESS FOR EVALUATING LIFE OF ARTICLE SUBJECTED TO THERMAL CYCLES BASED ON COMPARISON OF STRAIN RATES MEASURED UNDER EVALUATING CONDITIONS AND ACTUAL SERVICE CONDITIONS

BACKGROUND OF THE INVENTION

1. Field of the Invention

The present invention relates to a process for evaluating a thermal cycle life of an article to be subjected to a thermal cycle under actual service conditions, based on restraint rates at various points on the article.

2. Description of the Prior Art

A process for evaluating a thermal cycle life of an exhaust manifold subjected to a thermal cycle using, as parameters, an offset yield strength of the exhaust manifold at a lower limit temperature in the thermal cycle and an area of a plastic strain loop in a second thermal cycle, is disclosed in "Hitachi Metal Technical Report", Vol. 8, pp. 79–84. A process for evaluating a thermal cycle life of an exhaust manifold using a largest value of a plastic strain of the exhaust manifold as an evaluating parameter is disclosed in "Previous Print Issue, No.9833115 in Scientific Lecture Meeting by Society of Automotive Engineers of Japan, Inc.".

In the above conventional process, it is necessary to provide a thermal cycle under actual service conditions to the exhaust manifold to actually measure variations in strain and stress with the passage of time. However, when the highest temperature under the actual service conditions is high, the strain and stress of the exhaust manifold cannot be measured and for this reason, the evaluating parameter cannot be determined directly from a measured value. There is also a process involving the reproduction of the evaluating parameter using a simulation provided by a computer. However, in a state in which a measured value in an exhaust manifold cannot be obtained due to a high temperature, a simulation result cannot be collected and for this reason, an evaluating parameter having a high accuracy cannot be obtained.

SUMMARY OF THE INVENTION

The present invention has been accomplished with the above circumstance in view, and it is an object of the present invention to accurately evaluate a thermal cycle life of an exhaust manifold by obtaining a restraint rate as an evaluating parameter.

To achieve the above object, there is provided a process for evaluating a thermal cycle life of an exhaust manifold, which will be described below.

The present invention is directed to a process for evaluating a thermal cycle life of an article to be subjected to a thermal cycle under actual service conditions, based on restraint rates at various points on the article, comprising the steps of providing a thermal cycle of a temperature profile under evaluating conditions to the article, so that the temperature profile under actual service conditions and the temperature profile under the evaluating conditions satisfy the following condition expression:

$$|[t(x)-t_0]/[t(x=i)-t_0]-[T(x)-T_0]/[T(x=i)-T_0]| < E$$

wherein $t(x)$ is the temperature at a site X when at a high temperature in the thermal cycle under the actual service conditions; $t_0$ is the equalized temperature when at a low temperature in the thermal cycle under the actual service conditions; $t(x=i)$ is the temperature at a site i when at the high temperature in the thermal cycle under the actual service conditions; $T(x)$ is the temperature at the site X when at the high temperature in the thermal cycle under the evaluating conditions; $T_0$ is the equalized temperature when at the low temperature in the thermal cycle under the evaluating conditions; $T(x=i)$ is the temperature at the site i when at the high temperature in the thermal cycle under the evaluating conditions; and E is a predetermined value. The thermal cycle life of the article to be subjected to the thermal cycle under the actual service conditions is evaluated, based on the restraint rates determined in the temperature profile.

The term "evaluating conditions" means a temperature at which a restraint rate can be measured by a strain gauge, e.g., 300° C. The term "actual service conditions" means a temperature at which a restrained rate cannot be measured by the strain gauge, e.g., 600° C. to 750° C. The term "equalized temperature" when at the low temperature in the thermal cycle means ambient temperature, e.g., 25° C.

If the absolute value of a deviation between the standardized temperature profile $[T(x)-T_0]/[T(x=i)-T_0]$ of the article under the evaluation conditions and the standardized temperature profile $[t(x)-t_0]/[t(x=i)-t_0]$ of the article under the actual service conditions is smaller than the predetermined value E, it is ensured that a restraint rate η under the actual service conditions and a restraint rate η under the evaluating conditions are substantially equal to each other. Therefore, a restraint rate η of the article can be determined only by providing, to the article, the thermal cycle under the evaluating conditions in which a thermally expanded amount can be measured by the strain gauge, on condition that the absolute value of the deviation is smaller than the predetermined value, without providing, to the article, the thermal cycle under the actual service conditions in which it is difficult to measure a thermally expanded amount by the strain gauge due to a high temperature. Thus, the thermal cycle life of the article can be evaluated precisely based on the restraint rate η.

BRIEF DESCRIPTION OF THE DRAWINGS

The mode for carrying out the present invention will now be described by way of an embodiment shown in the accompanying drawings.

DETAILED DESCRIPTION OF THE PREFERRED EMBODIMENT

Figure 8:
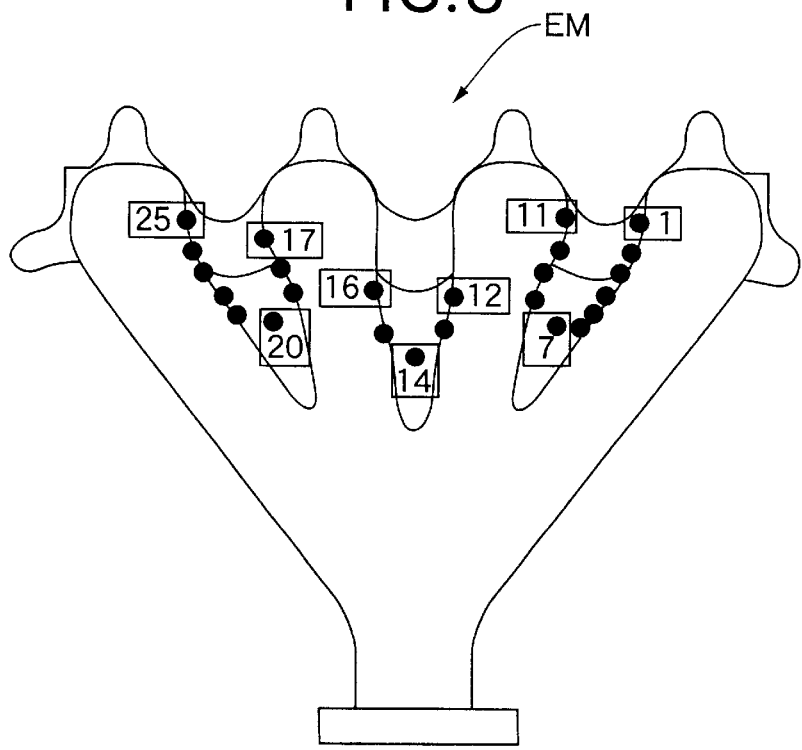
FIG. 8 is a diagram showing evaluation points on the exhaust manifold.

An article such as an exhaust manifold EM of an engine for an automobile, as shown in FIG. 8, is exposed to a high-temperature exhaust gas during operation of the engine and becomes heated, and is cooled down to a room ambient temperature upon stopping of the engine. For this reason, the article may be repeatedly subjected to a thermal cycle with temperature differences reaching several hundred degrees C, resulting in damage such as cracks generated in the article, in some cases. When the article is subjected to the thermal cycle, if the article is not restrained and is in a freely thermal expandable state, it is difficult to generate a thermal stress and hence, the thermal cycle life of the article is long. On the other hand, when the free thermal expansion of the article is restrained by another article, the thermal cycle life is shortened by the thermal stress generated by the thermal expansion. Therefore, the thermal cycle life of the article with respect to the thermal cycle can be evaluated using a restraint rate η indicative of a degree of restraint of the thermal expansion of the article as a parameter.

TABLE 1

| Element | C | Si | Mn | P | S | Mg |
|---|---|---|---|---|---|---|
| % by weight | 3.50 | 3.55 | 0.18 | 0.023 | 0.013 | 0.039 |

Figure 1:
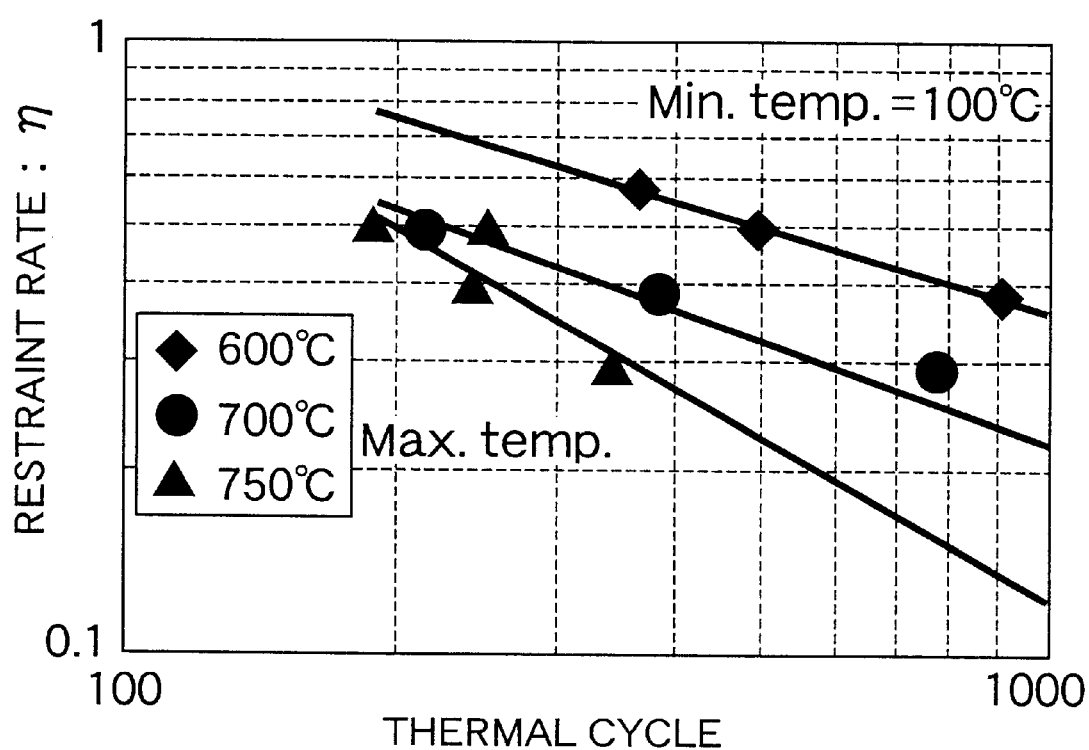
FIG. 1 is a graph showing how the thermal cycle life of an article is varied depending on the highest temperature and the restraint rate η in a thermal cycle.

FIG. 1 shows how the thermal cycle life of the article made using spheroidal graphite cast iron as a material shown in Table 1, is varied by the highest temperature in the thermal cycle and by the restraint rate η. The restraint rate η of the article is defined by the following equation:

$$\eta = \frac{\Delta Lt - \Delta L}{\Delta Lt} \quad (1)$$

wherein ΔL is the elongation under the restraint conditions, and ΔLt is the free elongation in a given variation in temperature.

As apparent from FIG. 1, as the highest temperature in the thermal cycle becomes higher, and as the restraint rate η of the article becomes higher, the thermal cycle life is shorter. Therefore, the thermal cycle life of the article can be evaluated using the highest temperature in the thermal cycle and the restraint rate η of the article as parameters.

To determine a restrain rate η defined in the equation (1), it is necessary to detect the free elongation ΔLt of the article in a given variation in temperature and the elongation ΔL of the article under the restraint conditions by a strain gauge. However, in a high-temperature state in which the highest temperature in the thermal cycle reaches, for example, 600° C. to 750° C., there is a problem that it is difficult to determine a restraint rate η, because a foil-type strain gauge cannot be used. Therefore, in the present invention, the restraint rate η of the article can be determined accurately to properly evaluate the thermal cycle life, while suppressing the highest temperature in the thermal cycle to a temperature at which the strain gauge can be used (e.g., the highest temperature is 280° C.). A technique for determining a restraint rate η, while suppressing the highest temperature in the thermal cycle to a temperature at which the strain gauge can be used will be described below.

Figure 2A:
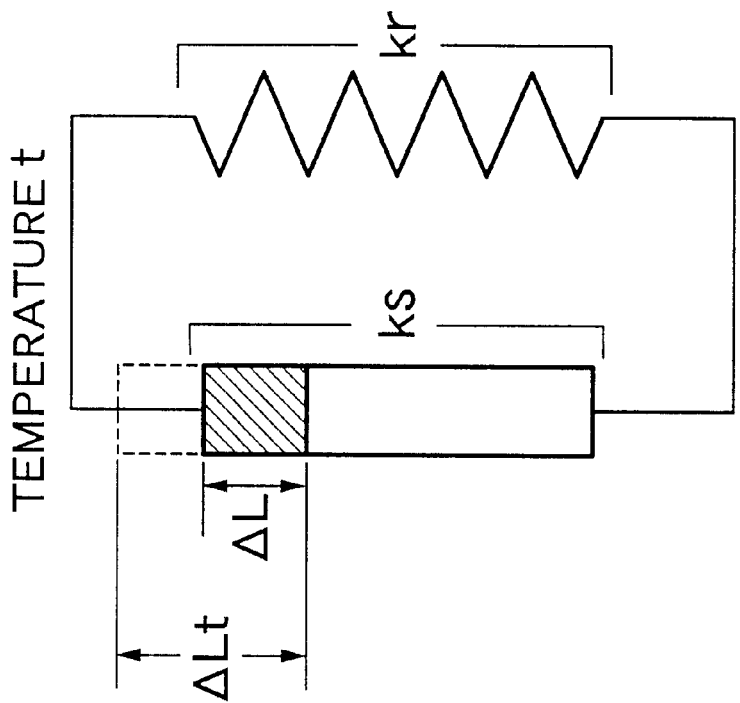
FIGS. 2A and 2B are diagrams each showing a model of a restrained state provided by a restraining spring kr and a restrained spring ks.

FIG. 2A shows a model in which a restrained spring Ks having a spring constant ks (the restrained spring will be indicated using its spring constant ks hereinafter) has been restrained by a restraining spring Kr having a spring constant kr (the restraining spring will be indicated using its spring constant kr hereinafter). When the restrained spring ks is heated from a state at a temperature $t_o$ shown in FIG. 2A to a state at a temperature t shown in FIG. 2B, the length of the restrained spring ks is increased from L to L+ΔL by the thermal expansion corresponding to a length ΔL.

At this time, the restraining spring kr is stretched by ΔL by the restrained spring ks and hence, a tensile force Pr applied to the restraining spring kr is provided according to the following equation:

$$Pr = kr \cdot \Delta L \quad (2)$$

wherein Pr is the force generated in the restraining spring, and kr is the spring constant of the restraining spring. On the other hand, the restrained spring ks should be thermally expanded by ΔLt in a non-restrained state, but can be thermally expanded by ΔL only under the influence of the restraining force of the restraining spring kr. If the non-restrained state is defined as a standard, the restrained spring ks is contracted by ΔLt−ΔL. Therefore, a compressing force Ps applied to the restrained spring ks is given according to the following equation:

$$Ps = -ks \cdot (\Delta L - \Delta Lt) \quad (3)$$

wherein Ps is the force generated in the restrained spring, and ks is the spring constant of the restrained spring.

Figure 2B:
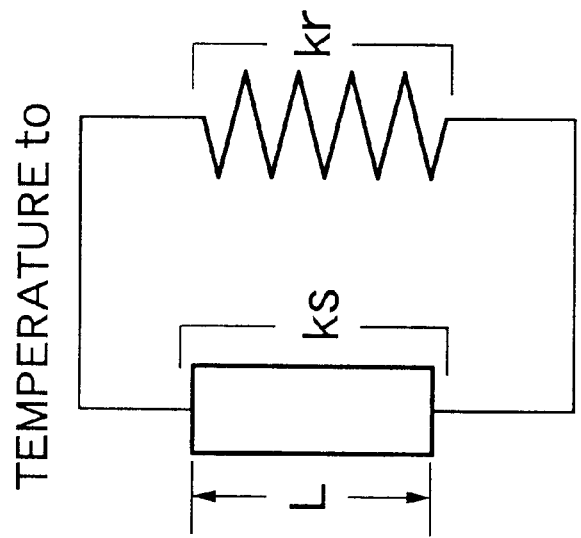
Figure 3:
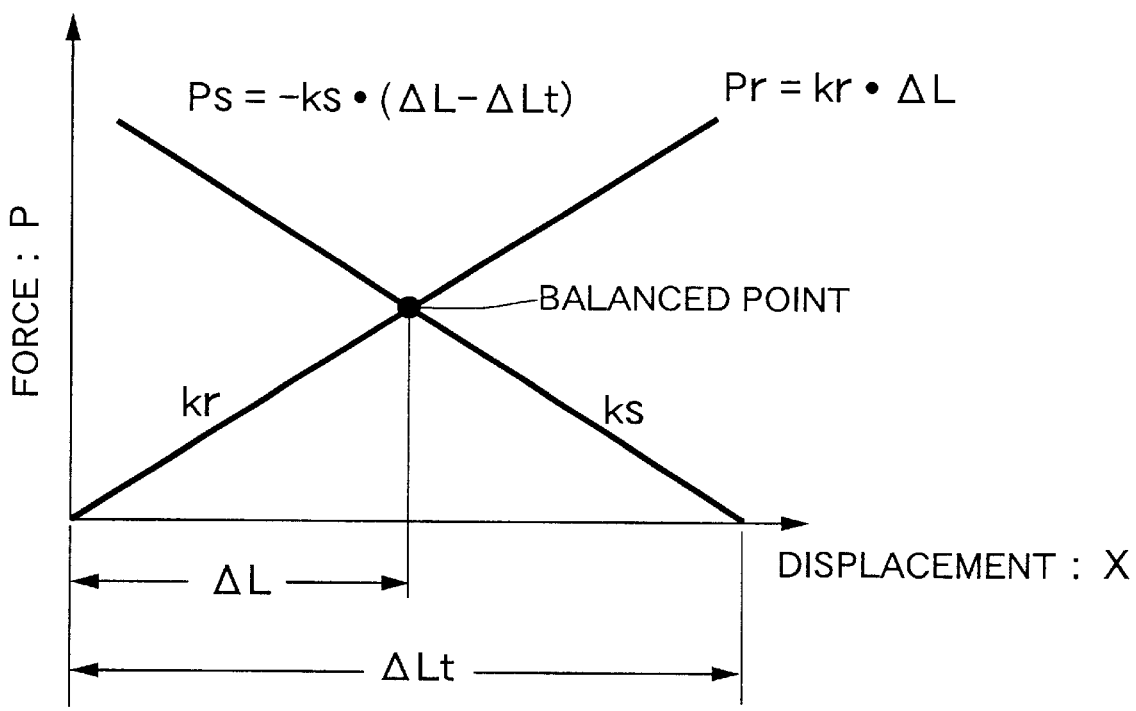
FIG. 3 is a diagram showing a force-balanced state in the restrained state model.

In a balanced state in FIG. 2B, the tensile force Pr applied to the restraining spring kr is equal to the compressing force Ps applied to the restrained spring ks, as shown in FIG. 3. Therefore, the following equation is established:

$$kr \cdot \Delta L = -ks \cdot (\Delta L - \Delta Lt) \quad (4)$$

When this equation is solved with respect to an elongation ΔL of the restrained spring ks, the following equation is provided:

$$\Delta L = \frac{ks}{kr + ks} \cdot \Delta Lt \quad (5)$$

Thus, when the equation (5) is placed into the equation (1), a restraint rate η is given according to the following equation:

$$\eta = \frac{\Delta Lt - \Delta L}{\Delta Lt} = \frac{\Delta Lt - \frac{ks}{kr+ks} \cdot \Delta Lt}{\Delta Lt} = \frac{1}{1 + \frac{ks}{kr}} \quad (6)$$

Here, the ratio of the spring constant ks of the restrained spring ks to the spring constant kr of the restraining spring kr is defined as follows:

$$a = \frac{ks}{kr} \quad (7)$$

When the equation (7) is placed into the equation (6), the restraint rate $\eta$ is represented by the following equation:

$$\eta = \frac{1}{1+a} \quad (8)$$

As apparent from the equation (8), the restraint rate $\eta$ is determined by a ratio a of the spring constant ks of the restrained spring ks to the spring constant kr of the restraining spring kr.

Figure 4:
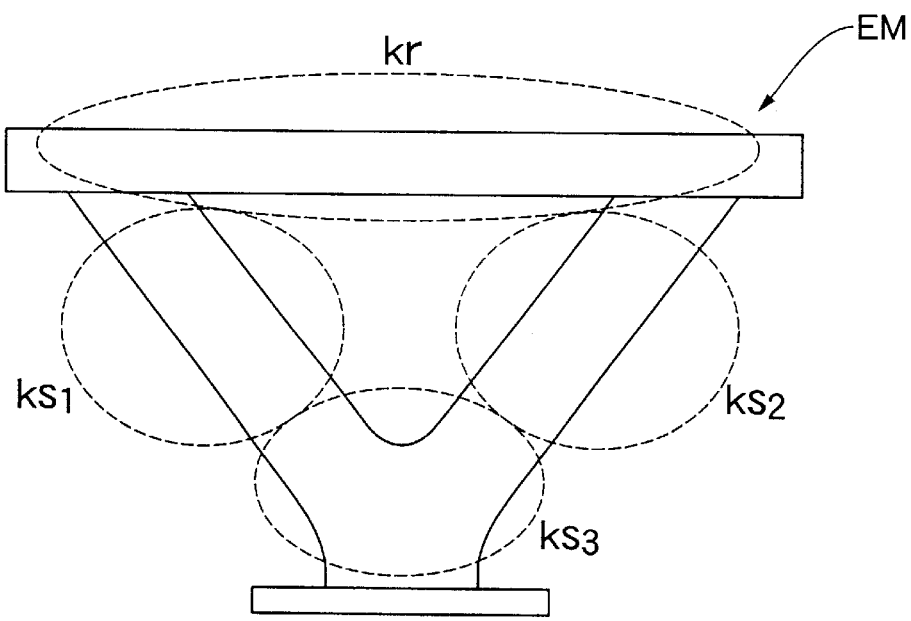
FIG. 4 is a diagram showing a model of a restrained state of an exhaust manifold.

FIG. 4 shows an exhaust manifold EM for a serial 2-cylinder engine. The exhaust manifold EM comprises a mounting flange coupled to a cylinder head, two simple pipe portions, and a collection portion at which the two simple pipe portions are collected together. The mounting flange constitutes a restraining spring kr, and the two simple pipe portions constitute two restrained springs $ks_1$ and $ks_2$. The collection portion constitutes a restrained spring $ks_3$. A configuration of the exhaust manifold EM represented in a spring model is shown in FIG. 5.

Figure 5:
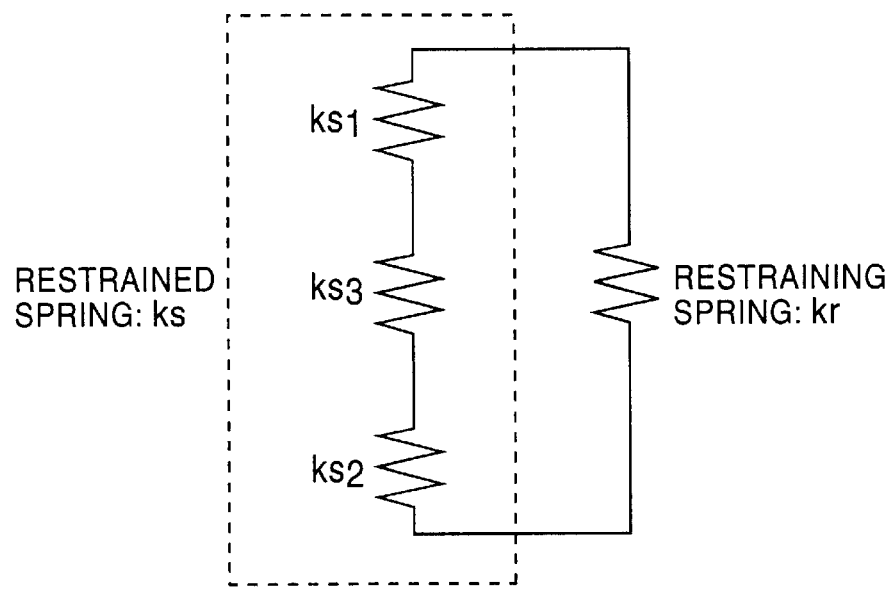
FIG. 5 is a diagram showing a spring model in the restrained state model.

The force P generated in the spring model in FIG. 5 is given according to the following equation (9) from the equations (2) and (5):

$$P = \frac{ks}{kr+ks} \cdot \Delta Lt \cdot kr \quad (9)$$

wherein P is the force generated in a spring system.

In the spring model shown in FIG. 5, the three restrained springs $ks_1$, $ks_2$ and $ks_3$ are connected in series to one another and hence, a force P represented in the equation (9) is applied to the every restrained springs $ks_1$, $ks_2$ and $ks_3$. Therefore, if the central restrained spring $ks_3$ is considered, a displacement $X_3$ is given according to the following equation (10):

$$X_3 = \frac{P}{ks_3} \quad (10)$$

$$= \frac{ks}{(k_r + k_s) \cdot ks_3} \cdot \Delta Lt \cdot kr$$

wherein $X_3$ is a displacement which occurs in the restrained spring $ks_3$. In this case, a restraint rate $\eta_3$ of the restrained spring $ks_3$ is given according to the following equation (11):

$$\eta_3 = \frac{X_3}{\Delta Lt_3} \quad (11)$$

wherein $\eta_3$ is the restraint rate of the restrained spring $ks_3$, and $\Delta Lt_3$ is the free thermal expansion coefficient of the restrained spring $ks_3$. If the equation (10) is placed into the equation (11) to rewrite the restraint rate $\eta_3$, the following equation is provided:

$$\eta_3 = \frac{1}{\Delta Lt_3} \cdot \frac{ks}{(kr+ks) \cdot ks_3} \cdot \Delta Lt \cdot kr = \quad (12)$$

$$\frac{\Delta Lt \cdot ks}{\Delta Lt_3 \cdot ks_3} \cdot \frac{kr}{kr+ks_3} = \frac{\Delta Lt \cdot ks}{\Delta Lt_3 \cdot ks_3} \cdot \eta_{TOTAL}$$

wherein $\eta_{TOTAL}$ is a restraint rate of the entire restrained spring.

In the equation (12), the free elongation $\Delta Lt$ in the given variation in temperature can be represented as a function of temperature as shown in the following equation:

$$\Delta Lt = \int \alpha \cdot \{(t(x)-t_0)\} \cdot dx \quad (13)$$

wherein $\alpha$ is a linear expansion coefficient, and t(x) is a function of temperature profile of the restrained spring.

It is considered that the linear expansion coefficient $\alpha$ is substantially constant in a defined range of temperature, and hence, the equation (13) is rewritten as follows:

$$\Delta Lt = \alpha \cdot \int \{(t(x)-t_0)\} \cdot dx \quad (14)$$

The free elongation $\Delta Lt_3$ in the given variation in temperature can be also represented as a function of temperature as shown in the following equation:

$$\Delta Lt_3 = \alpha \cdot (t_3 - t_0) \cdot L_3 \quad (15)$$

wherein $t_3$ is the temperature of the restrained spring $ks_3$, and $L_3$ is the length of the restrained spring $ks_3$.

Therefore, when equations (14) and (15) are placed into equation (12), the restraint rate $\eta_3$ is given according to the following equation (16):

$$\eta_3 = \frac{\Delta Lt \cdot ks}{\Delta Lt_3 \cdot ks_3} \cdot \eta_{TOTAL} = \quad (16)$$

$$\frac{\alpha \cdot \int \{t(x) - t_0\} \cdot dx}{\alpha \cdot (t_3 - t_0) \cdot L_3} \cdot \frac{ks}{ks_3} \cdot \eta_{TOTAL} = \frac{\int \{t(x) - t_0\} dx}{(t_3 - t_0) \cdot L_3} \cdot$$

$$\frac{ks}{ks_3} \cdot \eta_{TOTAL} = \frac{1}{L_3} \cdot \int \frac{\{t(x) - t_0\}}{t_3 - t_0} \cdot dx \cdot \frac{ks}{ks_3} \cdot \eta_{TOTAL}$$

In the equation (16), $L_3$, ks, $ks_3$ and $\eta_{TOTAL}$ are shape parameters for the exhaust manifold EM, and t(x) and $t_3$ are temperature parameters for the exhaust manifold EM. If the shape of the exhaust manifold EM is determined, the shape parameters $L_3$, ks, $ks_3$ and $\eta_{TOTAL}$ are determined reasonably, but the temperature parameters t(x) and $t_3$ depend on the temperature profiles for the exhaust manifold EM. Therefore, the restraint rate $\eta_3$ given according to the equation (16) depends on a standardized temperature profile determined from the temperature profile, namely, it depends substantially on a temperature profile $[t(x)-t_0]/(t_3-t_0)$ standardized by $t_3$ based on $t_0$.

Therefore, a restraint rate $\eta_3$ under actual service conditions can be determined by providing a temperature profile T(x) under evaluation conditions shown in the following equation:

$$\frac{t(x) - t_0}{t_3 - t_0} = \frac{T(x) - T_0}{T_3 - T_0} \quad (17)$$

Here, when the equation (17) is established, the following equation is established with respect to temperatures t(x=i) and T(x=i), at any site i, of t(x) and T(x).

$$\frac{t(x=i) - t_0}{t_3 - t_0} = \frac{T(x=i) - T_0}{T_3 - T_0} \quad (18)$$

wherein t(x=i) is the temperature, at the site i, of t(x), and T(x=i) is the temperature, at the site i, of T(x).

Thus, when opposite sides of the equation (17) are divided by opposite sides of the equation (18), the following equation is provided:

$$\frac{t(x) - t_0}{t(x=i) - t_0} = \frac{T(x) - T}{T(x=i) - T_0} \quad (19)$$

Therefore, a temperature in the standardization of the temperature profile may be the temperature t(x=i) or T(x=i) at any same site of t(x) and T(x).

Figure 6:
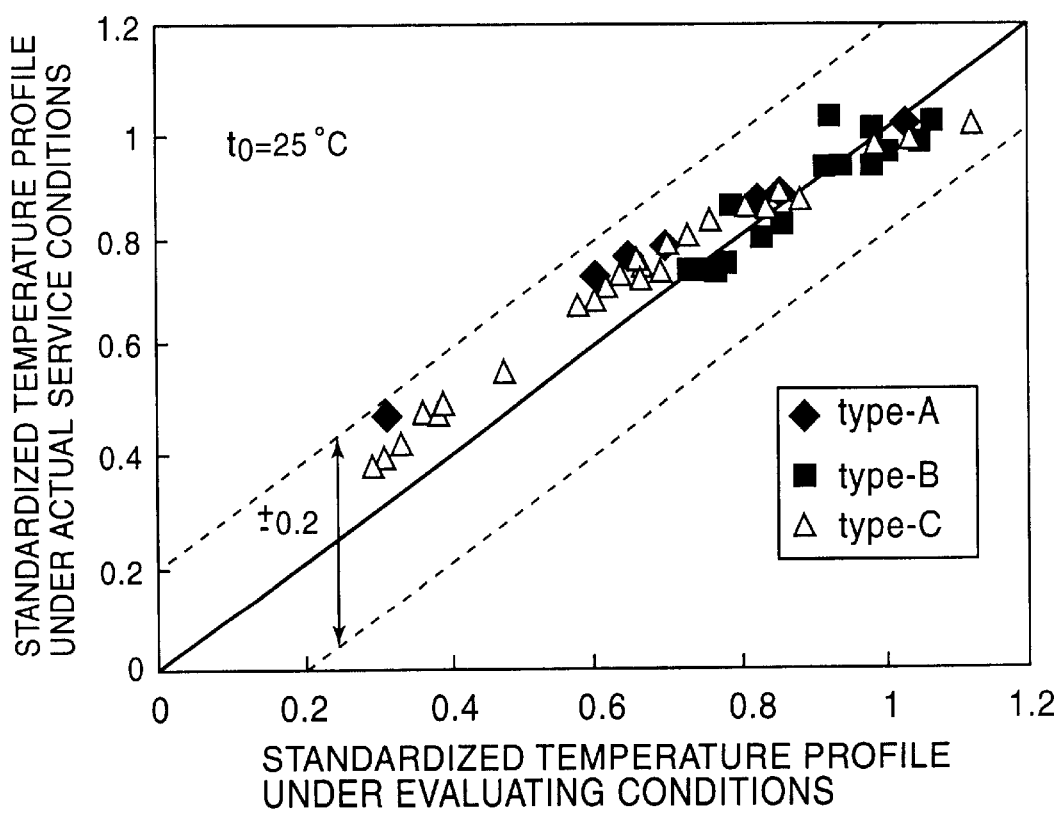
FIG. 6 is a graph for comparing standardized temperature profiles under actual service conditions and evaluation conditions.

The axis of ordinates in FIG. 6 is a standardized temperature profile $[t(x)-t_0]/[t(x=i)-t_0]$ calculated from a result of actual measurement of the temperature profile provided when an engine having the exhaust manifold EM mounted thereon has been operated under actual service conditions with a highest temperature of 750° C. The axis of abscissas in FIG. 6 is the standardized temperature profile $[T(x)-T_0]/[T(x=i)-T_0]$ calculated from the result of actual measurement of the temperature profile provided when the engine having the exhaust manifold EM mounted thereon has been operated under evaluation conditions with a highest temperature of 280° C.

As apparent from FIG. 6, the absolute value of the deviation between the standardized temperature profile $[T(x)-T_0]/[T(x=i)-T_0]$ under the evaluation conditions and the standardized temperature profile $[t(x)-t_0]/[t(x=i)-t_0]$ under the actual service conditions is always smaller than a predetermined value E (0.2) at each of various points, and the standardized temperature profile under the evaluation conditions and the standardized temperature profile under the actual service conditions coincide substantially with each other. Therefore, the standardized temperature profile $[T(x)-T_0]/[T(x=i)-T_0]$ under the evaluation conditions with the highest temperature of 280° C. can be constructed as corresponding to the substantially faithful reproduction of the standardized temperature profile $[t(x)-t_0]/[t(x=i)-t_0]$ under the actual service conditions with the highest temperature of 750° C.

Figure 7:
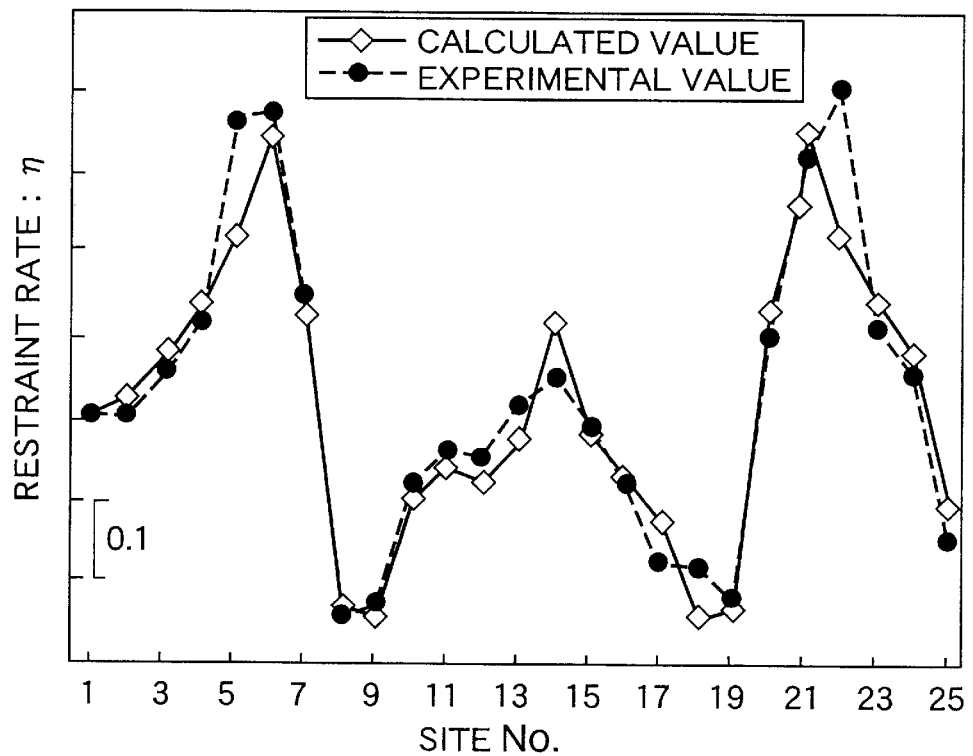
FIG. 7 is a graph showing experimental values and calculated values of restraint rate η.

FIG. 7 shows restraint rates η at fifty-five evaluation points on the exhaust manifold EM shown in FIG. 8, wherein the broken line indicates experimental values determined from results of the actual measurement of thermally expanded amounts under the evaluation conditions by a strain gauge, and the solid line indicates calculated values determined by determining restraint rates η under the actual service conditions by a computer simulation. It is confirmed from FIG. 7 that the restraint rates η determined under the evaluation conditions have a satisfactory accuracy.

Therefore, when the restraint rate $\eta_3$ under the actual service conditions is determined, it is not necessarily required that the actual service conditions be reproduced. If the restraint rate $\eta_3$ under the evaluation conditions such that the following equation is established is determined, such restraint rate $\eta_3$ coincides with the restraint rate $\eta_3$ under the actual service conditions. The highest temperature of the exhaust manifold EM under the evaluation conditions is suppressed to 280° C., the amount of exhaust manifold thermal expansion at each of its points can be measured by the strain gauge, and the restraint rate $\eta_3$ of the exhaust manifold EM at each of the points can be calculated from the measurement result.

$$\left| \frac{t(x) - t_0}{t(x=i) - t_0} - \frac{T(x) - T_0}{T(x=i) - T_0} \right| < 0.2 \quad (20)$$

Figure 9:
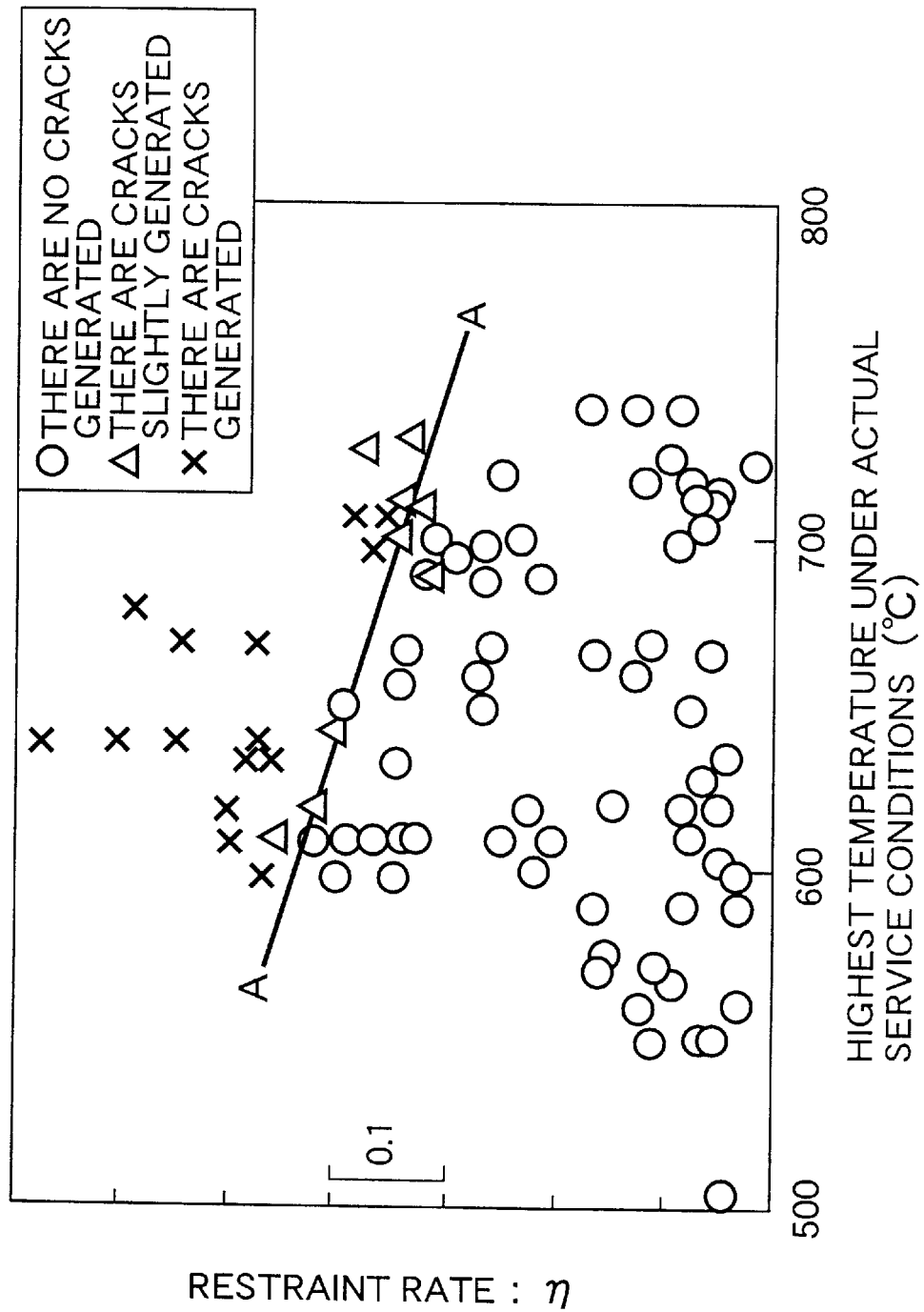
FIG. 9 is a graph showing the relationship between the highest temperature and the restraint rate η under the actual service conditions and the presence or absence of cracks generated.

FIG. 9 shows the result provided when it has been confirmed whether cracks have been generated when the exhaust manifold EM having a restraint rate η determined in the above-described manner, has been used under actual service conditions with the highest temperature varied to various values. As apparent from FIG. 9, in a region below the line A—A where the restraint rate η is small, no cracks have been generated in the exhaust manifold EM, and in the region above the line A—A where the restraint rate η is large, cracks have been generated. From this, it can be confirmed that the thermal cycle life of the exhaust manifold EM can be evaluated precisely by the restraint rate η determined by the technique in the present invention.

Although the embodiment of the present invention utilizing the exhaust manifold EM of the engine has been described, it will be understood that the present invention is applicable to the evaluation of the thermal cycle life of each of various other articles used under conditions in which the thermal expansion is restrained.

Figure 10:
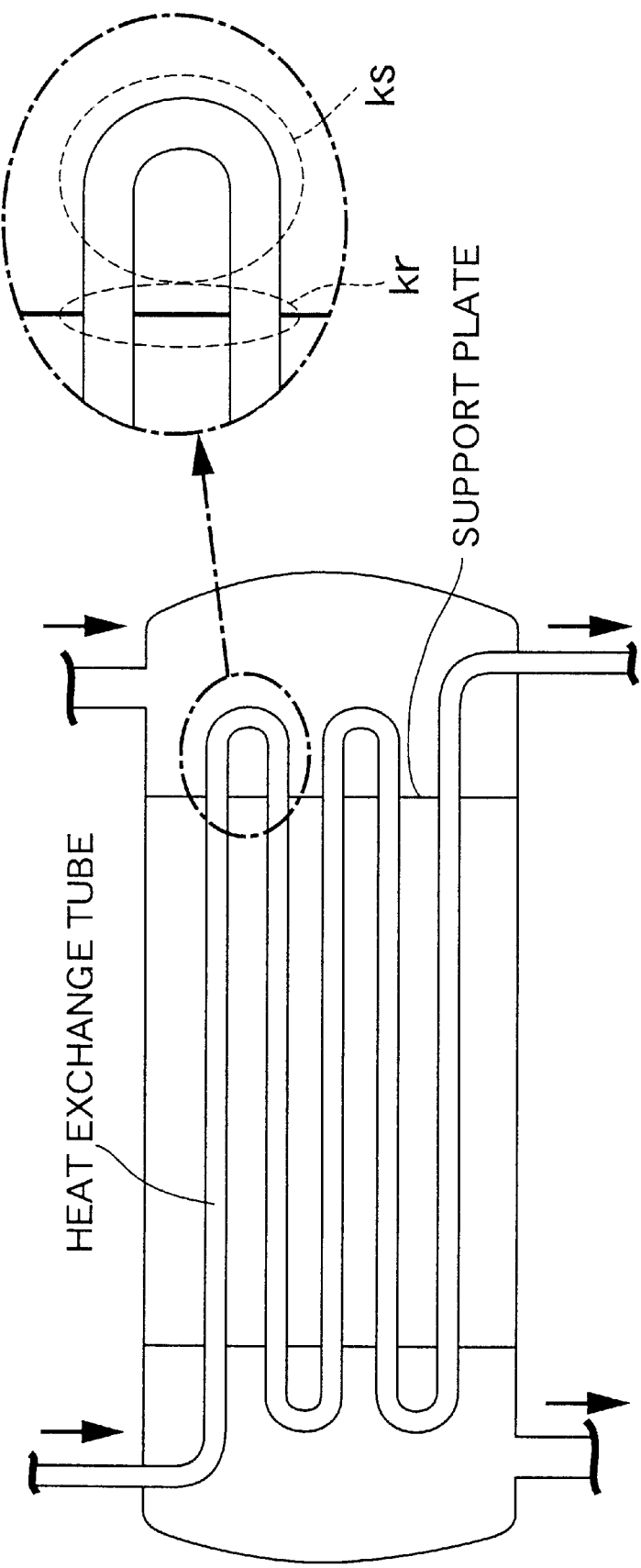
FIG. 10 is a diagram showing an embodiment of the present invention applied to a heat exchanger.
Figure 11:
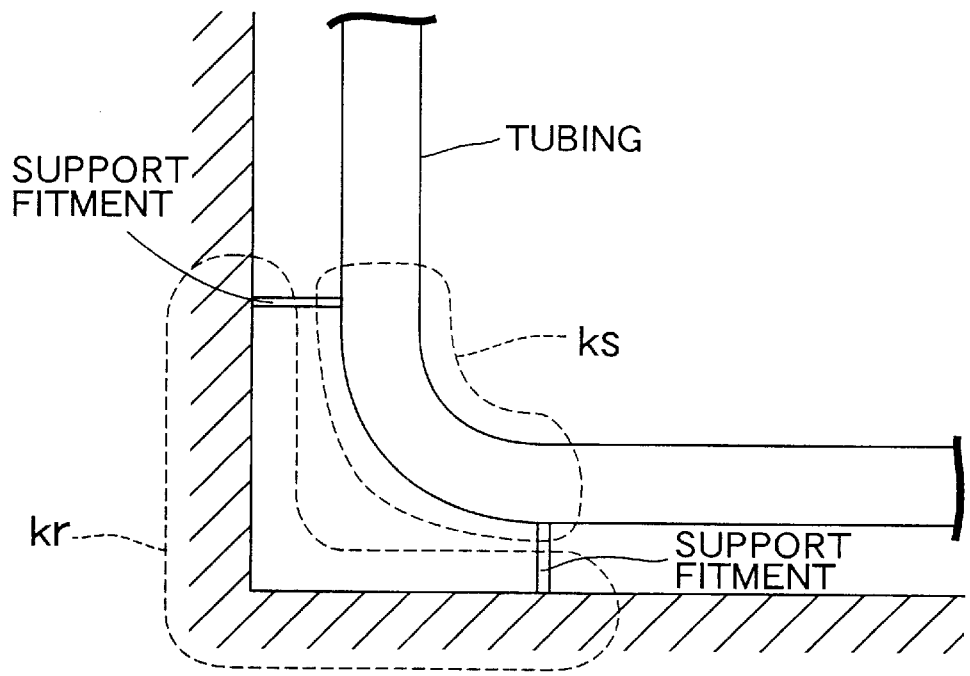
FIG. 11 is a diagram showing an embodiment of the present invention applied to a boiler tubing.
Figure 12:
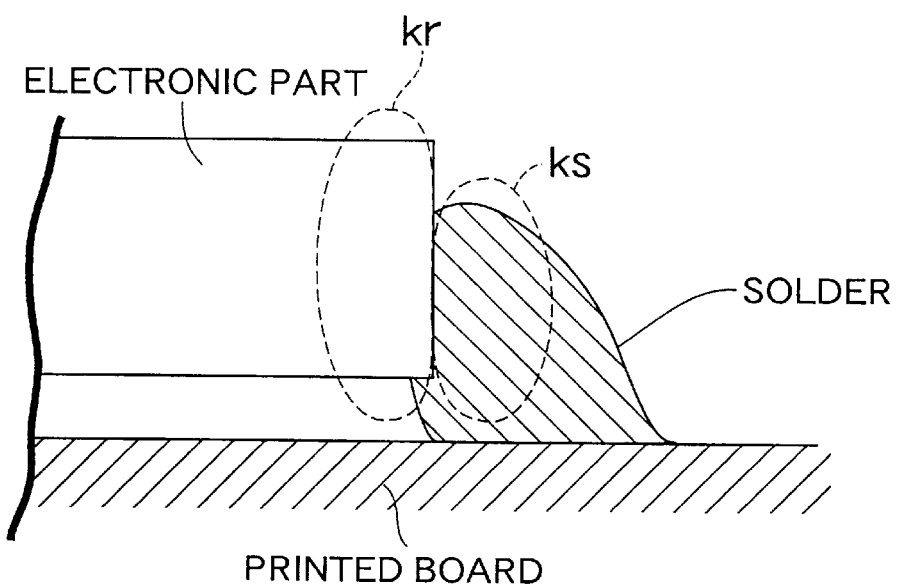
FIG. 12 is a diagram showing an embodiment of the present invention applied to the soldering of an electronic part.
Figure 13:
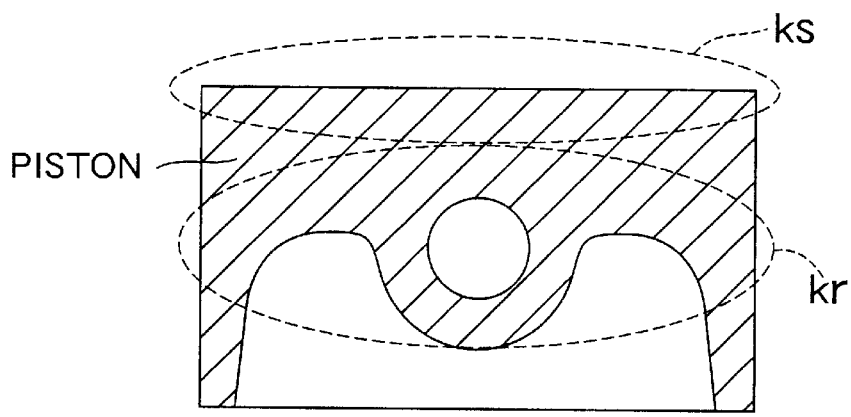
FIG. 13 is a diagram showing an embodiment of the present invention applied to a piston of an engine.
Figure 14:
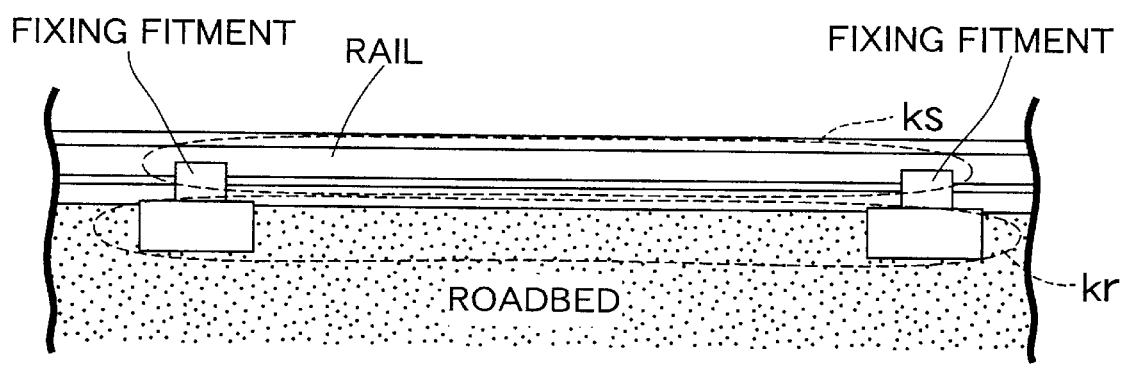
FIG. 14 is a diagram showing an embodiment of the present invention applied to a rail for a railroad.
Figure 15:
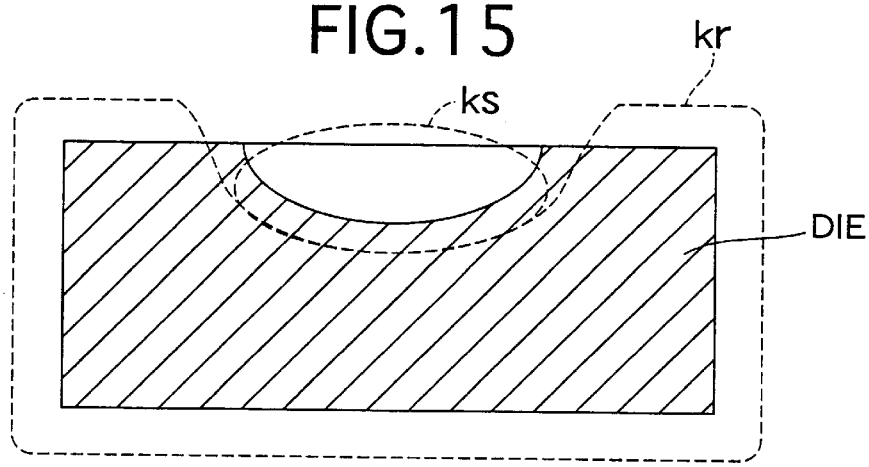
FIG. 15 is a diagram showing an embodiment of the present invention applied to a hot forging die.
Figure 16:
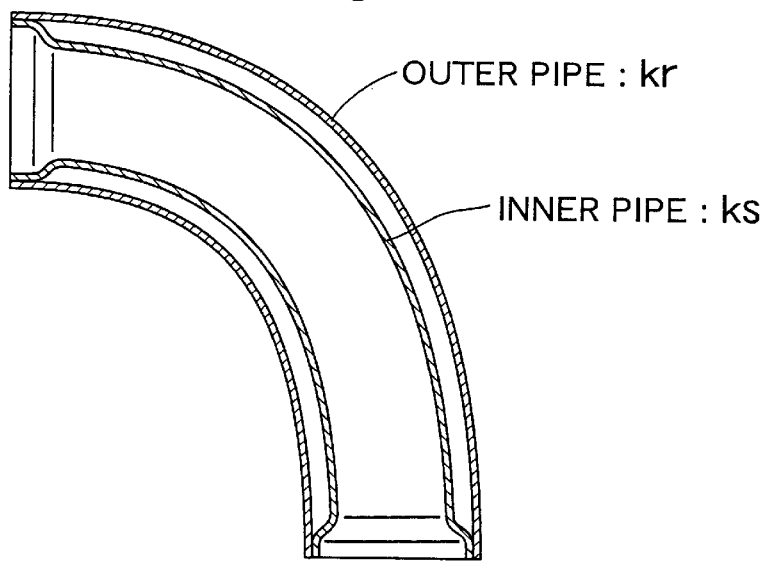
FIG. 16 is a diagram showing an embodiment of the present invention applied to a double-structure exhaust pipe.
Figure 17:
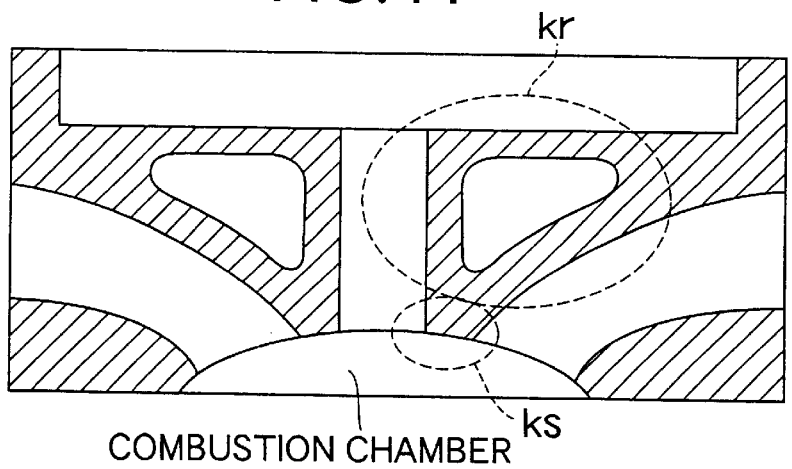
FIG. 17 is a diagram showing an embodiment of the present invention applied to a cylinder head of an engine.

FIG. 10 shows an embodiment of the present invention applied to a heat exchanger; FIG. 11 shows an embodiment of the present invention applied to a boiler tubing; FIG. 12 shows an embodiment of the present invention applied to the soldering of an electronic part; FIG. 13 shows an embodiment of the present invention applied to a piston of an engine; FIG. 14 shows an embodiment of the present invention applied to a rail for a rail road; FIG. 15 shows an embodiment of the present invention applied to a hot forging die; FIG. 16 shows an embodiment of the present invention applied to a double-structure exhaust pipe; and FIG. 17 shows an embodiment of the present invention applied to a cylinder head of an engine. In each of these embodiments, ks designates a restrained portion, and kr designates a restraining portion.

The predetermined value defining the absolute value of the deviation between the standardized temperature profiles under the actual service conditions and under the evaluating conditions, is set at 0.2 in the preferred embodiment described above, but it may be changed, because it is varied depending on t(x=i) and T(x=i).

If the present invention is applied to a computer simulation, the number of temperature boundary conditions can be reduced and hence, the simulation can be achieved more easily.

As discussed above, the restraint rate η of the article can be determined only by providing, to the article, the thermal cycle under the evaluating conditions in which the thermally expanded amount can be measured by the strain gauge, on condition that the absolute value of the deviation is smaller than the predetermined value, without providing, to the article, the thermal cycle under the actual service conditions in which it is difficult to measure the thermally expanded amount by the strain gauge due to the high temperature. Thus, the thermal cycle life of the article can be evaluated precisely based on the restraint rate η.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A process for evaluating a thermal cycle life of an article to be subjected to a thermal cycle under actual service temperature conditions at which restrained rates cannot be measured by a strain gauge, based on restraint rates measured at various points on the article under evaluating temperature conditions at which restrained rates can be measured by the strain gauge, wherein said evaluating temperature conditions are lower than said actual service temperature conditions, the process comprising the steps of:

(a) providing a thermal cycle of a temperature profile under said evaluating temperature conditions to the article, wherein the temperature profile under said actual service temperature conditions and the temperature profile under the evaluating temperature conditions satisfy the following condition, $$\|[t(x)-t_0]/[t(x=i)-t_0]-[T(x)-T_0]/[T(x=i)-T_0]\| < E$$

wherein:

$t(x)$ is the temperature at a first site when at a high temperature in the thermal cycle under the actual service temperature conditions;

$t_0$ is the equalized temperature when at a low temperature in the thermal cycle under the actual service temperature conditions;

$t(x=i)$ is the temperature at a second site when at the high temperature in the thermal cycle under the actual service temperature conditions;

$T(x)$ is the temperature at the first site when at the high temperature in the thermal cycle under the evaluating temperature conditions;

$T_0$ is the equalized temperature when at the low temperature in the thermal cycle under the evaluating temperature conditions;

$T(x=i)$ is the temperature at the second site when at the high temperature in the thermal cycle under the evaluating temperature conditions;

and E is a predetermined value;

(b) measuring restraint rates at the first and second sites in the temperature profile; and (c) evaluating the thermal cycle life of the article to be subjected to a thermal cycle under said actual service temperature conditions, based on the measured restraint rates.

2. A process as set forth in claim 1, wherein E=0.2.

* * * * *